United States Patent [19]
Hutchins

[11] Patent Number: 5,039,678
[45] Date of Patent: Aug. 13, 1991

[54] METHOD OF INCREASING CRANIAL VESSEL PROLIFERATION BY ADMINISTERING NIMODIPINE

[75] Inventor: Phillip M. Hutchins, Winston-Salem, N.C.

[73] Assignee: Wake Forest University, Winston-Salem, N.C.

[21] Appl. No.: 328,111

[22] Filed: Mar. 23, 1989

[51] Int. Cl.$^5$ ............................................. A61K 31/44
[52] U.S. Cl. .................................................... 514/356
[58] Field of Search ........................................ 514/356

Primary Examiner—Stanley J. Friedman
Attorney, Agent, or Firm—Sprung Horn Kramer & Woods

[57] ABSTRACT

This invention relates to a method of increasing cranial arterioles in warm-blooded animals comprising administering an effective amount of the compound having the formula 1,4-dihydro-2,6-dimethyl-4-(3'-nitrophenyl)-pyridine-3-$\beta$-methoxyethyl ester)-5-(isopropyl ester), to said animals to achieve vessel proliferation.

4 Claims, 7 Drawing Sheets

METHOD OF INCREASING CRANIAL VESSEL PROLIFERATION BY ADMINISTERING NIMODIPINE

BRIEF DESCRIPTION OF THE INVENTION

This invention relates to a method for increasing vessel growth of cranial vessels including cranial arterioles comprising administering an effective amount to achieve vessel proliferation of the compound having the formula 1,4-dihydro-2,6-dimethyl-4-(3'-nitrophenyl)-pyridine-3-,$\beta$-methoxyethyl ester) hereinafter referred to as nimodipine.

Unsymmetrical esters of 1,4-dihydropyridine-dicarboxylic acids, processes for their production and their use as coronary and antihypertensive agents is disclosed in U.S. Pat. No. 3,799,934. U.S. Pat. No. 3,932,645 includes the mixture of nimodipine and an inert carrier and the use of the compound to effect coronary vascular dilatation. Additionally, it has been found that nimodipine has an advantageous action on cerebral circulatory disturbances. U.S. Pat. No. 4,406,906 discloses a method of combating pathologically reduced cerebral functions and performance weaknesses, cerebral insufficiency and disorders in cerebral circulation and metabolism.

Nimodipine has been the subject of considerable investigation. Studies conducted by Harper et al, J. Cereb. Blood Flow Metab. 1: 49-356, 1981 indicated that nimodipine crosses the blood-brain barrier. The dilatory effects of nimodipine are known to be more selective to the cerebral vessels that hydralazine. Harris et al, Stroke 13: 759-766, 1982); Kazda and Towart, Acta Neurochirurgica 63: 259-265, 1982; Towart et al, Arzneimittelforsch 32: 338-346, 1982. Further, nimodipine exerts a cerebral vasodilatory effect without increasing intracranial pressure. Hadley et al, J. Neurosurg. 66: 387-393, 1987.

Surprisingly, the compound, nimodipine used according to the present invention, exhibits, in doses administered over time, new vessel growth. The long-term effect of nimodipine on the pial microcirculation is causing vessel growth. Vessel growth includes an increase in the diameter of the vessel, and an increase in the number of vessels.

It is recognized that vessel proliferation is a function of delivering an effective amount of nimodipine for a sufficient duration. It is within the scope of this invention that an effective amount of nimodipine may be delivered utilizing sustained release systems. Such sustained release systems are well known in the prior art, for example, U.S. Pat. No. 4,765,989 discloses an osmotic system for delivering drugs at a broad range of drug delivery rates and can deliver the drugs according to a predetermined drug release pattern to a receipt over time.

This invention also provides a method for long-term, longitudinal observations of pial microvasculature in conscious rats comprising the steps of:
(a) surgically introducing a cranial window into the skull of said rats,
(b) inserting a catheter into the abdominal aorta and connecting the catheter to a hemodynamic monitoring system, and
(c) allowing the rats to stabilize prior to testing, wherein said cranial window includes a flat cover slip resting on a cranial ledge, said cover slip is sealed over an accurately cut opening in the skull with superglue.

The chronic cranial window preparation allows repeated measurements of the same pial vessels in unanesthetized rats for several weeks, and correlation with 24 hour monitoring of hemodynamic variables. Nimodipine (20 mg) or placebo was given via two subcutaneous pellets. Large arterioles dilated 26% and 16%, at hour 1 and in the chronic epoch, respectively ($p<0.02$). There was an increase in number of small arterioles throughout the whole observation period with the maximal increment of 47% ($p<0.05$) in the chronic epoch (6-13 days). Maximal vasodilation with 10% $CO_2$ indicated that the increase in number of small arterioles after administering nimodipine was not due to the opening of previously closed vessels. Separate estimation of the total length of small arterioles and venules demonstrated increases of 47% and 23% in the chronic epoch, respectively ($p<0.001$). These increases are entirely due to the increases in the numbers of vessels, because the average length of the small vessels did not change significantly. This suggests a reduced cerebral vascular resistance by new vessel growth. Our data demonstrate that the administration of nimodipine (20mg) is potent in dilating pial arterioles in the short-term without affecting systemic arterial pressure, and that its long-term effect results in new vessel growth.

The present invention finds application in all mammalian species, including both humans and animals. The suprising advantageous properties are illustrated in the detailed description of the invention.

DETAILED DESCRIPTION

Until very recently, the main application of calcium entry blockers was restricted to the cardiovascular system outside the brain, especially in the treatment of angina pectoris, hypertension and certain types of cardiac arrhythmias. However, great interest has been aroused since their introduction in the early eighties for the prevention or treatment of certain neurological disorders. (Auer L. M., Z. Ito, A. Suzuki, and H. Ohta. Prevention of symptomatic vasospasm by topically applied nimodipine. Acta Neurochirurgia 63: 297–302, 1982; Steen P.A., L. A. Newberg, J. H. Milde, and J. D. Michenfelder. Nimodipine improves cerebral blood flow and the neurologic recovery after complete cerebral ischemia in the dog. J. Cereb. Blood Flow Metab. 3: 38–43, 1983; White B. C., C. D. Winegar, R. F. Wilson, P. J. Hoehner, and J. H. Trombley Jr. Possible role of calcium channel blockers in cerebral resuscitation: a review of the literature and systhesis for future studies. Crit. Care Med. 11: 202–207, 1983.)

Nimodipine seems to be the most potent of all pyridine derivatives yet described as calcium entry blockers with respect to its effects on cerebral vasculature. (Kazda S., F. Hoffmeister, B. Garthoff, and R. Towart. Prevention of the postischaemic impaired reperfusion of the brain by nimodipine. Acta Neurol. Scand. 60 (Suppl. 72): 302–303, 1979; Towart R., E. Wehinger, H. Meyer, and S. Kazda. The effects of nimodipine, its optical isomers and metabolites on isolated vascular smooth muscle. Arzneimittelforsch 32: 338–346, 1982.) Experimentally it has been shown to possess cerebral protective properties, (Meyer F. B., R. E. Anderson, T. L. Yaksh, and T. M. Sundt Jr. Effect of nimodipine on intracellular brain pH, cortical blood flow, and EEG in experimental focal cerebral ischemia. J. Neurosurg. 64: 617–626, 1986; Milde L. N., J. H. Milde, and J. D. Michenfelder. Delayed treatment with nimodipine improves cerebral blood flow after complete cerebal ischemia in the dog. J. Cereb. Blood Flow Metab. 6: 332–337, 1986; Steen P. A., S. E. Gisvold, J. H. Milde, L. A. Newberg, B. W. Scheithauer, W. L. Lanier, and J. D. Michenfelder. Nimodipine improves outcome when given after complete cerebral ischemia in primates. Anesthesiology 62: 406–414, 1985; Steen P. A., L. A. Newberg, J. H. Milde, and J. D. Michenfelder. Nimodipine improves cerebral blood flow and neurologic recovery after complete cerebral ischemia in the dog. J. Cereb. Blood Flow Metab. 3: 38–43, 1983; White B. C., C. D. Winegar, R. F. Wilson, P. J. Hoehner, and J. H. Trombley Jr. Possible role of calcium blockers in cerebral resuscitation: a review of the literature and systehsis for future studies Crit. Care Med. 11: 202–207, 1983.) and widely employed as a vasodilator to treat vasospasm following subarachnoid hemorrhage in patients, (Allen, G. S., H. S. Ahn, T. J. Preziosi, R. Battye, S. C. Bone, S. N. Chou, D. L. Kelly, B. K. Weir, R. A. Crabbe, P. J. Lavik, S. B. Rosenbloom, F. C. Dorsey, C. R. Ingram, D. E. Mellits, L. A. Bertsch, D. P. J. Boisvert, M. B. Hundley, R. K. Johnson, J. A. Strom, and C. R. Transou. Cerebral arterial spasm—A controlled trial of nimodipine in patients with subarachnoid hemorrhage. N. Engl.J. Med. 308: 619–624, 1983; Grotenhuis J. A., W. Bettag, B. J. O. Fiebach, and K. Dabir. Intracarotid slow bolus injection of nimodipine during angiography for treatment of cerebral vasospasm after SAH. J. Neurosurg. 61 231–240, 1984.) and also in surgery. (Auer L. M. Preventive nimodipine and acute aneurysm surgery. Heading for the control of complications after aneurysmal subarachnoid hemorrhage. Neurochirurgia (Stuttg) 28 Suppl. 1: 87–92, 1984; Auer L.M., L. Brandt, U. Ebeling, and J. Gilsbach. Nimodipine and early aneurysm operation in good condition SAH patients. Acta Neurochirurgia (Wien) 82 7–13, 1986; Auer L. M., Z. Ito, A. Suzuki, and H. Ohta. Prevention of symptomatic vasospasm by topically applied nimodipine. Acta Neurochirurgia 63 297–302, 1982.) It appears to reduce or alleviate the occurrence of vasospasm following subarachnoid hemorrhage. (Allen, G. S., H. S. Ahn, T. J. Preziosi, R. Battye, S. C. Bone, S. N. Chou, D. L. Kelly, B. K. Weir, R. A. Crabbe, P. J. Lavik, S. B. Rosenbloom, F. C. Dorsey, C. R. Ingram, D. E. Mellits, L. A. Bertsch, D. P. J. Boisvert, M. B. Hundley, R. K. Johnson, J. A. Strom, and C. R. Transou. Cerebral arterial spasm—A controlled trial of nimodipine in patients with subarachnoid hemorrhage. N. Engl. J. Med. 308: 619–624, 1983; Auer L. M. Preventive nimodipine and acute aneurysm surgery. Heading for the control of complications after aneurysmal subarachnoid hemorrhage. Neurochirurgia (Stuttg) 28 Suppl. 1: 87–92, 1985; Auer L.M., L. Brandt, U. Ebeling, and J. Gilsbach. Nimodipne and early aneurysm operation in good condition SAH patients. Acta Neurochirurgia (Wien) 82: 7–13, 1986; Grotenhuis J. A., and W. Bettag. Prevention of symptomatic vasospasm after SAH by constant venous infusion of nimodipine. Neurological Research 8: 243–249, 1986; Steen P. A., S. E. Gisvold, J. H. Milde, L. A. Newberg, B. W. Scheithauer, W. L. Lanier, and J. D. Michenfelder. Nimodipine improves outcome when given after complete cerebral ischemia in primates. Anesthesiology 62: 406–414, 1985.) However, controversies still exist. (Gisvold S. E., and P. A. Steen. Drug therapy in brain ischaemia. Br. J. Anaesth. 57: 96–109, 1985; Harris R. J., N. M. Branston, L. Symon, M. Bayhan, and A. Watson. The effects of a calcium antagonist, nimodipine, upon physiological responses of the cerebral vasculature and its possible influence upon focal cerebral ischaemia. Stroke 13: 759–766, 1982.) Some studies indicate that nimodipine may not reduce the incidence or severity of cerebral vasospasm as demonstrated by angiography, (Grotenhuis J. A., and W. Bettag. Prevention of symptomatic vasospasm after SAH by constant venous infusion of nimodipine. Neurological Research 8: 243–249, 1986.) or by another method. (Vibulsresth S., W. D. Dietrich, R. Busto, and M. D. Ginsberg. Failure of nimodipine to prevent ischemic neuronal damage in rats. Stroke 18: 210–216, 1987.) Since brain tissue does not lend itself to in vivo observations, direct evidence regarding the long-term ability of nimodipine to reduce cerebrovascular resistance under normal and pathological conditions is lacking. Therefore, the present study was undertaken using the chronic cranial window technique to correlate the long-term effects of this drug on the pial vessels with the systemic circulation of unanesthetized rats.

Materials and Methods

The experimental procedures followed National Institutes of Health guidelines and were approved by the Animal Care and Use Committee of the Bowman Gray School of Medicine of Wake Forest University.

Experimental Protocol

Fifteen Sprague-Dawley rats with a mean body weight of 303.2+9.8 grams were used. Animals were randomly divided into a nimodipine-treated group (n=10) and a placebo group (n=5). Three or four days after the cranial window surgery was performed, a catheter was inserted into the abdominal aorta and connected to a 24-hour hemodynamic monitoring system. A second recovery period of three or four days was allowed for the systemic hemodynamic status and cerebral microvasculature to stabilize prior to the experiment. On experiment day 0, photographs of the pial microvasculature in the cranial window were taken as a control and then, immediately afterward, two nimodipine (10mg/tablet) or placebo pellets were implanted subcutaneously in the nape of the neck with a very sharp scalpel and a forceps. The nimodipine and placebo tablets were obtained from Innovative Research of America, Rockville, Md. The manufacturer presents data showing a constant, even release of the drug over 21 days. After pellet implantation, serial color photographs were obtained at hour 1, 3 and 6 for documenting acute vascular changes. Similar photographs of day 1, 2, 3, 6 and 13 were made to document the long-term effects of the drug. All pellet implantation and photographic procedures were done with the arterial line connected to the monitoring system and the animals in a completely conscious state.

In order to discern the possibilities of vessel growth and/or the opening of previously closed vessel as the cause of the vessel number 1, increase, additional 6 nimodipine rats underwent a $CO_2$ study, in which microvasculature measurements under higher magnification were performed before and after 10% $CO_2$ was inhaled for 5 min. at the baseline and on day 13.

Cranial Window Preparation

Animals were anesthetized using a 1:1 mixture of xylazine (20 mg/ml) and ketamine hydrochloride (100 mg/ml) at an intramuscular dose of 0.1 ml/100 gm body weight, and maintained with intraperitoneal injections of pentobarbital sodium (0.05 ml/100 gm) as needed. The skin over the dorsal surface of the skull was shaved and cleaned with an antimicrobial agent Betadine solution. Di-Trim (Syntex Animal Health, Inc., West Des Moines, Iowa) of 0.1 ml/100 gm body weight was given subcutaneously to prevent infection. The animal's head was mounted in a steriotaxic apparatus. Surgery was carried out under rigid aseptic conditions. A 3 cm oval mid-sagittal incision was made over the frontal and parietal portions of the skull. The soft tissues were reflected laterally to the temporal crest by blunt dissection and retracted with two mosquito hemostats. The pericranium was scraped off the skull. The bone surface was cleaned and dried with gauze. A circle 8 mm in diameter was outlined with a 7 mm metal cylinder and a sterile lead pencil.

The following steps were carried out under a surgical microscope. The skull was opened with an air-turbine dental drill with a fine-toothed burr 0.5 mm in diameter. Drilling was done perpendicularly along the drawn circular line. In order to avoid thermal injury, the drilled field was cooled frequently by dripping artificial cerebrospinal fluid during the vertical drilling. This also washed out the bone dust. As more holes were drilled, a circular groove was gradually formed. The depth of the groove, the perpendicularity of the groove wall and the diameter of the outer border of the groove circle were frequently checked and corrected when necessary. The objective was to make a circular opening with a diameter exactly 8 mm. Impending penetration of the inner table of the skull was detected by cautious pressure with a fine probe. Penetration of the bone was usually indicated by the appearance of a small amount of clear fluid at the bottom of the groove. When the bone flap yielded to cautious pressure at several points, no further drilling was needed.

Before removing the bone flap, a shelf about 0.5 mm wide was carefully made along the outer border of the groove using the dental burr. The depth of the shelf varied along the circle, depending on the convexity of the skull. In most situations it was deeper cephalically and caudally, and very shallow laterally. Occasionally there was no need to drill laterally as the cover slip could be supported without any gap between the slip and bone.

The circularly cut bone was gently lifted with a very fine blade, and carefully removed from the underlying adhering dura using the blade and sharpened forceps. All bone debris was carefully removed with tiny forceps. The cranial window, cut from Thermanox ™ (Miles Scientific, Naperville, IL) tissue culture cover slip to a diameter exactly 9 mm was tested for appropriate fit. The shelf was adjusted, if necessary, before the dura was opened.

Cutting the dura called for great care, as the exposed brain is very vulnerable and bleeds at the slightest injury. With the fine tip of a curved hook tangential to the surface, a slip was torn in the dura between the border of the sagittal sinus and the edge of the skull opening. It was essential to verify that no vessel was attached to the dura at the point of opening. Vannas scissors were inserted through the slip to extend the opening radially, and then the dura was completely removed. The medial flap of the he dura was retracted and cut with special care because tributaries of the sagittal sinus sometimes cross the subarachnoid space to enter the dura at some distance from the sinus. After the dura was removed, the pial surface was always kept moist with artificial cerebrospinal fluid.

The external bone edge of the craniotomy was checked for dryness and the cover slip gently placed over the bone opening and held firmly in position on the bone flange. A small amount of histo-compatible cyanocrylic glue was applied over the juncture between the cover slip and bone. Finally all layers of scalp tissues were sewn together with 3-0 silk sutures leaving the cranial window exposed.

The rat was then returned to its cage for recovery. All rats recovered quickly and usually appeared completely normal by the second post-operative day.

Abdominal Aortic Cannulation and Hemodynamic Monitoring

The method for abdominal aortic cannulation is similar to that by Weeks. (Weeks, J. R., and J. A. Jones. Routine direct measurement of arterial pressure in unanesthetized rats. Proc. Soc. Exp. Biol. Med. 104: 646–648, 1960.) The arterial catheter surrounded by stainless steel spring stock was connected to a flow-through swivel, blood pressure transducer and microperfusion pump (1.7 ml/24 hours—heparinized aline, 30 International Units/ml). This system allowed continuous registration of systolic and diastolic pressures, mean arterial pressure and heart rate. These hemodynamic variables were continually sampled (38,016 samples per minute) and computed each minute. The one minute averages were displayed on a video monitor. Hourly, 24 hours and light/dark cycle averages were saved to a dot matrix printer and diskette for future analysis. Since arterial blood pressure varies with the time in a light-/dark cycle, we selected the same hourly values during the last 3 control days to serve as a control for hour 1, 3 and 6 blood pressures. For daily blood pressure comparison, the mean of the 24 hour average values during the last 3 control days was used as a control.

Cranial Window Photography

Thirty-five millimeter photography was performed in the following manner. The rat (with the arterial line still connected to the monitoring system) was taken out of the cage and placed on the top cover of the cage. The animal was loosely restrained with the head held still by a gloved hand, leaving cranial window exposed. Most rats were quescent during this procedure. The cranial window was photographed using a Nikon F3 camera with a 105 mm Micro Nikkor lens and two PN 11 extension rings. A synchronized electronic flash mounted at the end of the lens was used as the primary light source. A fiber optic light placed approximately 2 cm above the window was also used to indicate possible light reflections produced by the electronic flash. The electronic flash eliminated artifacts due to slight movement and vibration of the field. Three radially located points on the pial microvasculature were determined to be in focus before the photograph was taken. The 35 mm photograph, taken on Kodock VRG-100 film, was enlarged to $11 \times 14$ inches without loss of appreciable definition. Using this criteria vessel images in all areas of the picture were usually sharp and of high quality.

Measurements of the Pial Vessels

To avoid bias all vessel measurements were performed in a blind fashion. For convenience and increased accuracy, computerized analyses of the pial vessels were different between the large and small vessels. Large arterioles were those with an average control diameter of 35 microns, small arterioles, 20 microns; large venules, 70 microns and small venules, 25 microns. For the large vessels, the same vessel was measured over the 9 time points. For the small vessels, all the vessels in a certain area were followed for the same 9 time points. Arterioles were easily distinguishable from venules on the following points. First, arterioles were normally a brighter red color than venules, Secondly, venules were wider than arterioles, Thirdly, arterioles were usually superficial to the venule. And lastly, venules could be traced into a tributary of the superior longitudinal sinus. Pial microvascular measurements were made on an $11 \times 11$ inch square digitizing tablet with 0.001 inch resolution (Digi-Pad Model 5, GTCO Corp., Rockville, Md.). The photographs and digitizer were calibrated to a known distance between the two furthest color dots drawn previously on the cover slip. The vessels in the photographs were digitized and the computer calculated the average diameter, length and number of each individual vessel category. The vessel wall was invisible; therefore, the diameter measured was the internal diameter of the vessel or the outer margin of red cell column.

Statistical Analysis

Data were averaged for each of the variables measured at each time point. Statistical analysis was performed using absolute values, while data were expressed as percentage of baseline to give a better demonstration of the effect of the drug over time.

Changes from baseline immediately following administration of nimodipine (hour 1) were examined using paired t test. In order to discern the general trend of alterations over the entire time course, the nine time points were grouped into four epochs: baseline, acute (hour 1, 3 and 6), intermediate (day 1, 2 and 3) and chronic (day 6 and 13). A repeated measures analysis of variance was performed to assess the differences between the baseline and any of these three post-treatment epochs. The statistical significance level of 0.05 was accepted as indicating significant differences.

Results

There were no significant intergroup (nimodipine vs placebo) differences with respect to initial body weights ($303.7 \pm 11.9$ grams vs $302.2 \pm 19.4$ grams) and 24 hour mean arterial pressure ($110.4 \pm 3.7$ mmHg vs $102.7 \pm 2.1$ mmHg). However, the initial heart rate was significantly ($p < 0.05$) different between the two groups (Table 1). Since heart rate is a variable prone to change, this small difference was not deemed important.

No significant intergroup differences in mean arterial blood pressure and heart rate were seen throughout the whole observation period (Table 1). Blood pressure and heart rate went up in both groups during the first several hours after implantation of the pellets (probably because of the stress of handling during implantation and photography). Both parameters returned to control levels by day 1. There were no significant changes in blood pressure thereafter in the nimodipine group. Blood pressures in the placebo group were still significantly higher than their own controls at day 6 and 13. Thee was a tendency to decrease heart rate with time in both groups.

Figure 1:
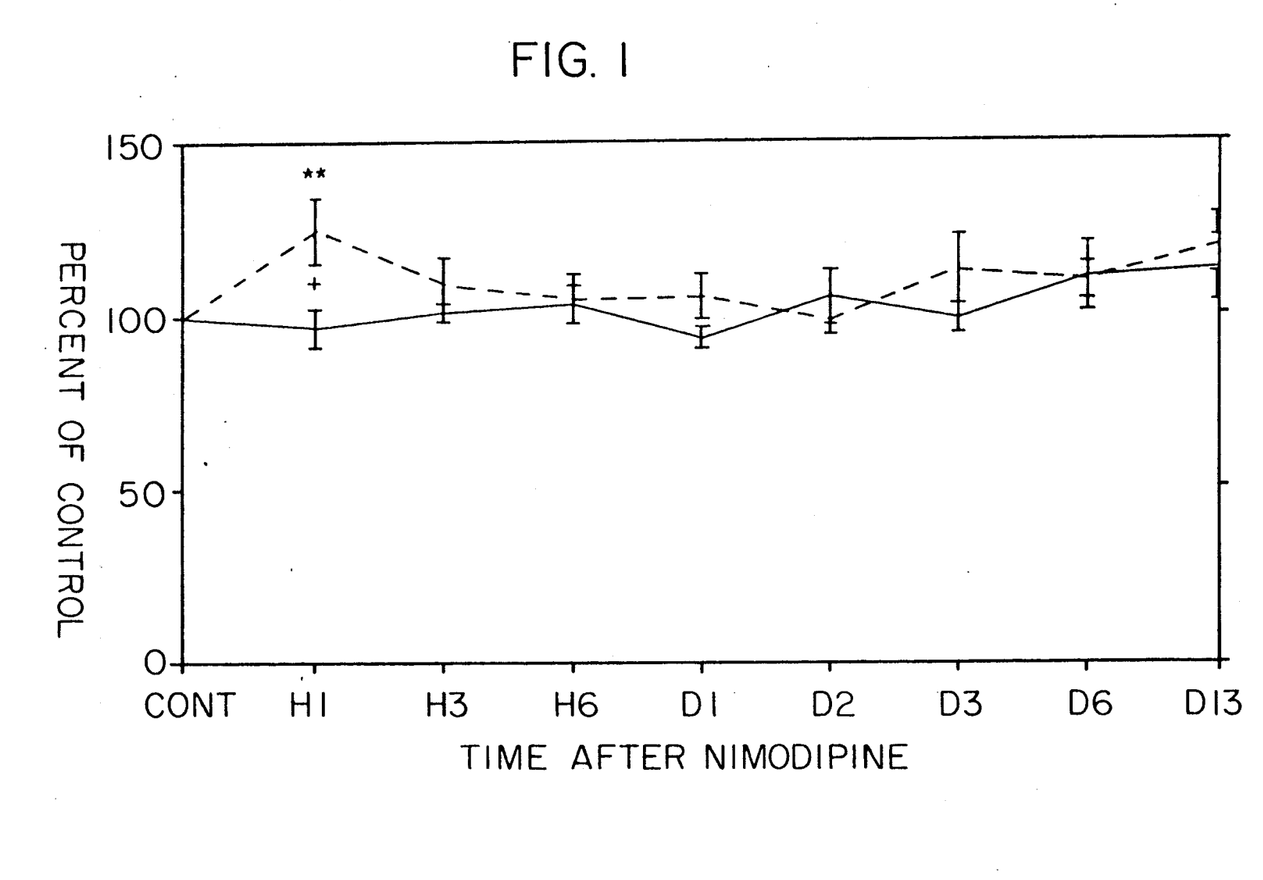
FIG. 1 is a graph demonstrating the effect of nimodipine (dashed line) on diameters of the rat pial large arterioles over 13 days (D). A 26% dilation (intra-group, $p<0.02$; inter-group, $p<0.05$) at hour (H) 1 and a 16% dilation (intra-group, $p<0.02$) in the chronic epoch (D6-13) were observed. Note no significant changes were seen in the placebo (solid line) group. Bars indicate standard error of the mean. Intra-group (vs baseline): **, $p<0.02$; Inter-group:+, $p<0.05$.
Figure 2:
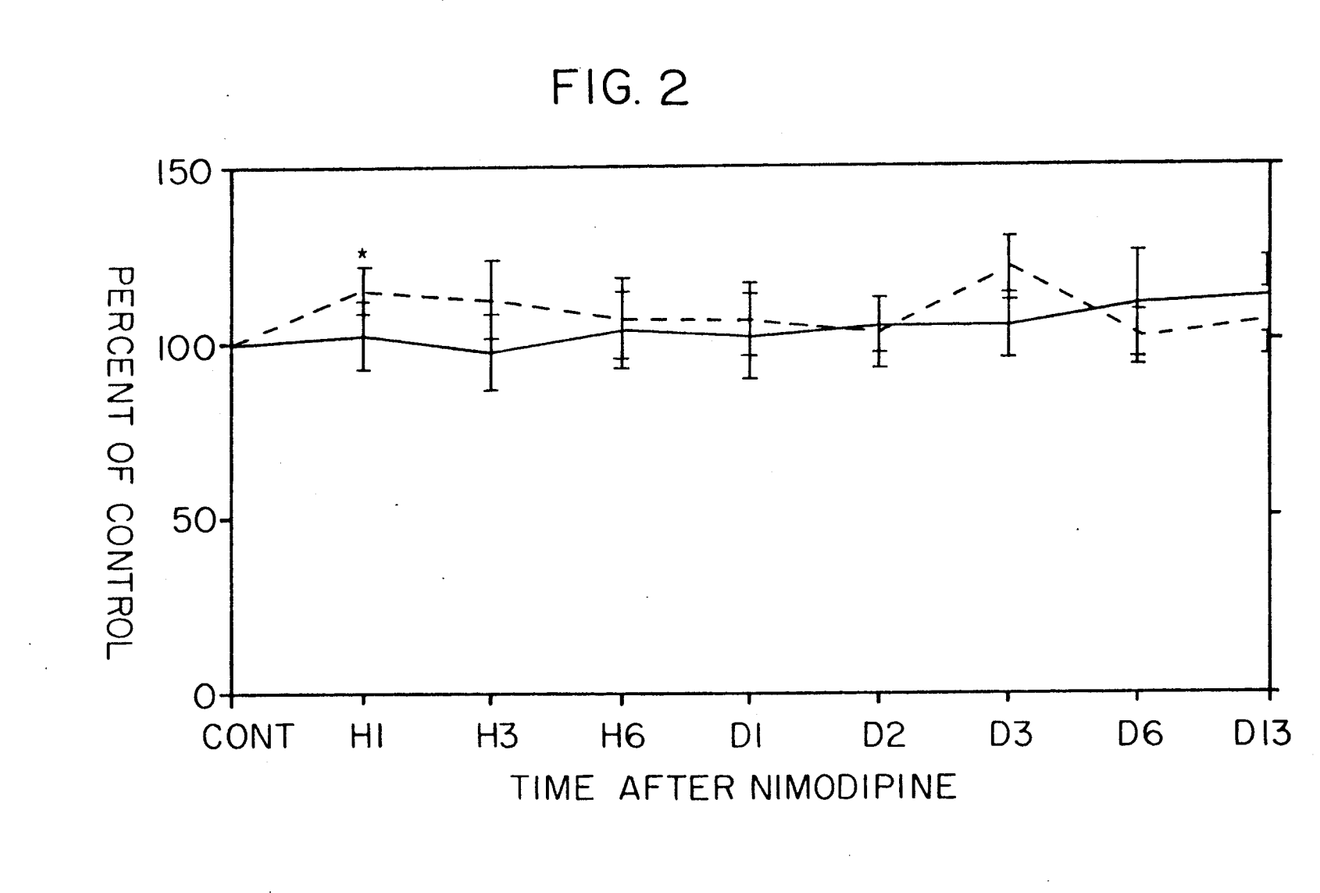
FIG. 2 is a graph demonstrating the effect of nimodipine on diameters of the rat pial small arterioles over 13 days. There were 16% ($p<0.05$) and 11% ($p<0.001$) dilations at H 1 and in the intermediate epoch (D1-3), respectively. Note no significant changes were seen in the placebo group. Intra-group (vs baseline): *, $p<0.05$. For the other notations see FIG. 1.

After pellet implantation, the large arterioles of the nimodipine group exhibited a 26% dilation at hour 1 (intragroup $p < 0.05$), which returned to control by day 2. However, dilation was subsequently observed from day 3 through day 13, with a 16% ($p < 0.02$) dilations in the chronic epoch, which was not significantly different from changes in the placebo group (FIG. 1). A similar dilatory trend existed with the small arterioles. They dilated 16% ($p < 0.05$) and 11% ($p < 0.001$) to hour 1 and in the intermediate epoch, respectively (FIG. 2). No significant large or small arteriolar diameter changes were seen in the placebo group (FIGS. 1 and 2).

Figure 3:
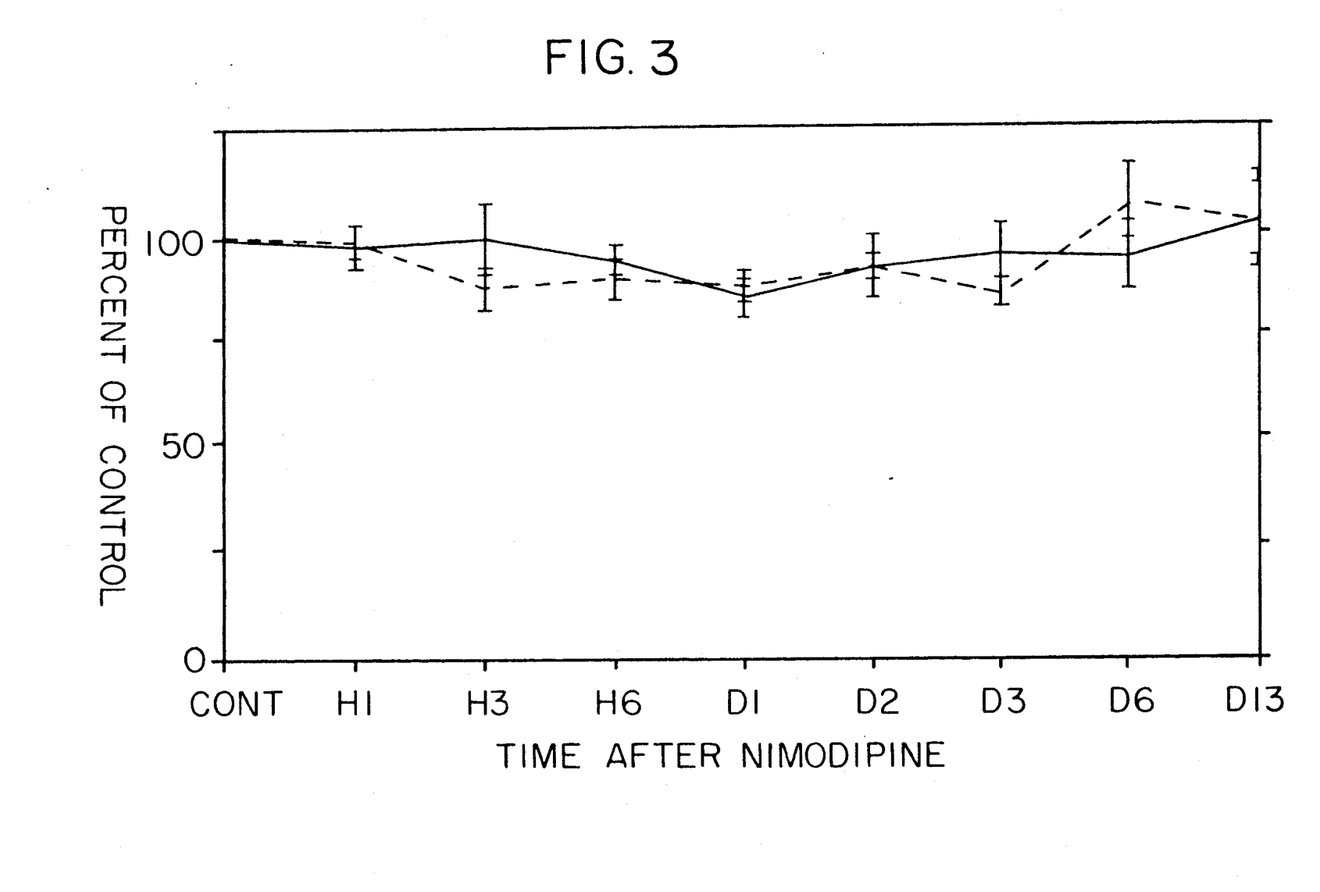
FIG. 3 is a graph demonstrating the effect of nimodipine on diameters of the rat pial large venules over 13 days. There was a gradual reduction in diameter with a maximum reduction of 11% ($p<0.01$) in the intermediate epoch. Note no marked changes were seen in the placebo group. For notations see FIGS. 1 and 2.
Figure 4:
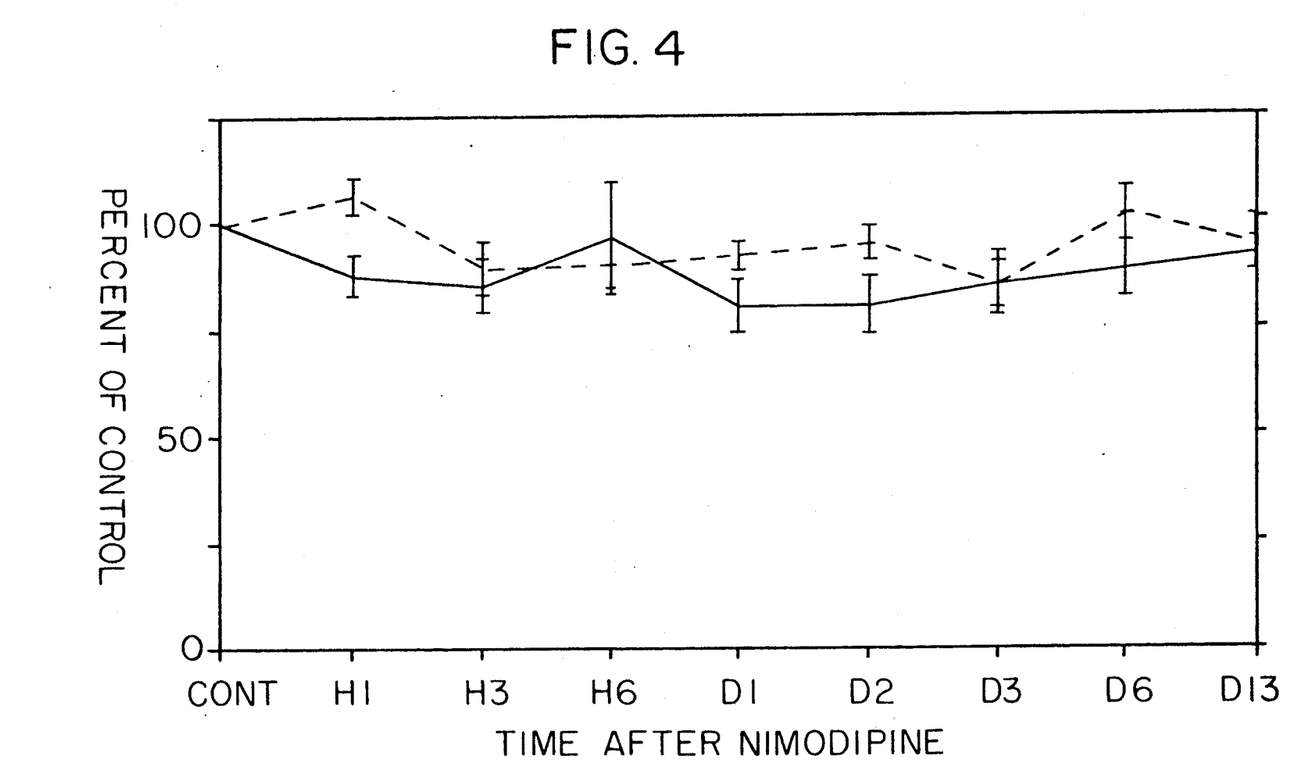
FIG. 4 is a graph demonstrating the effect of nimodipine on diameters of the rat pial small venules over 13 days. Small venules showed less consistent reductions in diameter compared with the placebo group. For notations see FIG. 1.

Large venules showed a gradual reduction in diameter with a maximum reduction of 11% ($p < 0.01$) in the intermediate epoch and then tended to increase their diameters. There were no marked changes in the placebo group (FIG. 3). Small venules showed less consistent reductions in diameter compared with the placebo group (FIG. 4), possibly because of the effectiveness of nimodipine in offsetting the pressure-related reduction in diameter of small venules.

Figure 5:
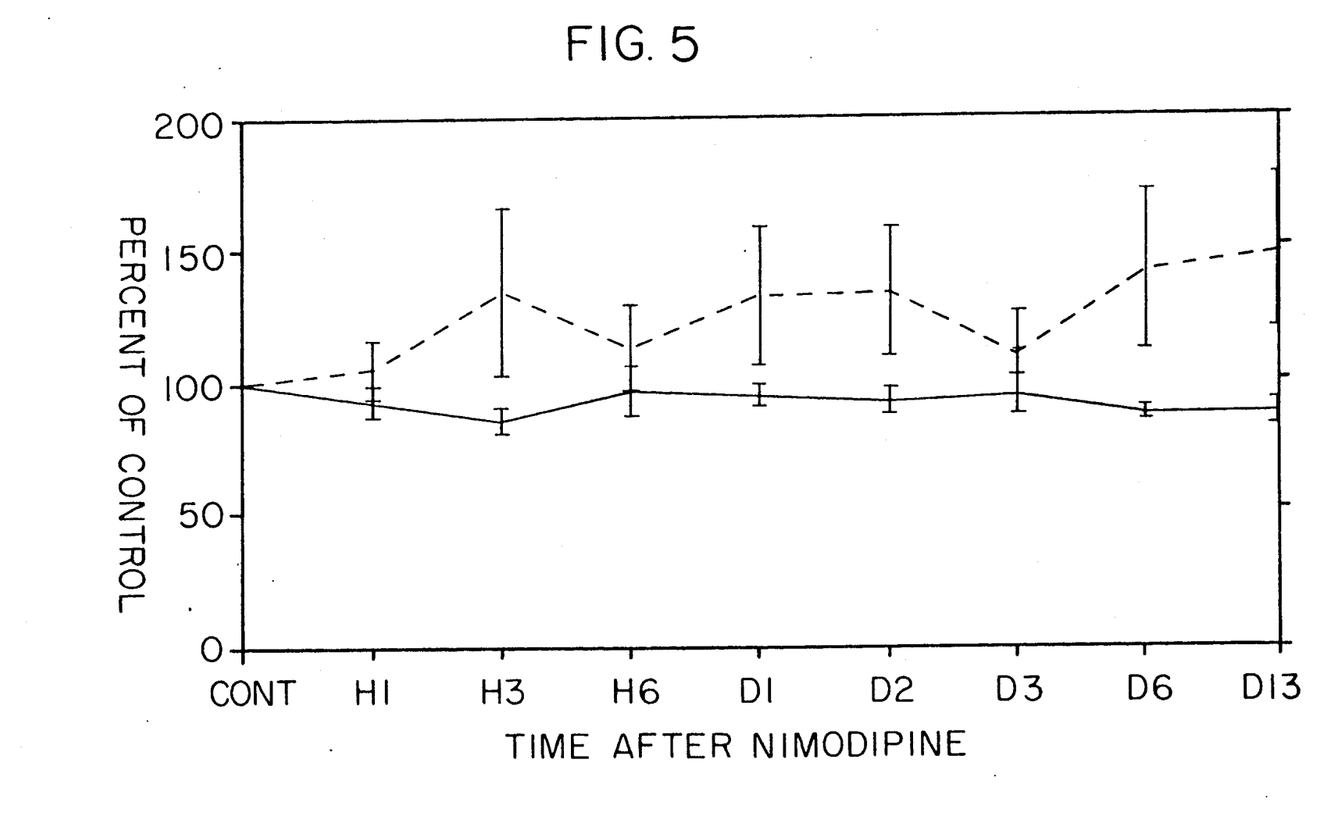
FIG. 5 is a graph demonstrating the effect of nimodipine on number of the rat pial small arterioles over 13 days. There was an increase in the number of small arterioles over the entire course with the maximal increment of 47% ($p<0.05$) in the chronic epoch (6-13 days). Note the number of small arterioles in the placebo group decreased. For notations see FIG. 1.

There was an increase in the number of small arterioles throughout the whole observation period with the maximal increment of 47% ($p < 0.05$) in the chronic epoch. The placebo group exhibited a modest decrease in arteriolar number (FIG. 5). There were no appreciable differences seen in the number of large arterioles, large venules or small venule of either nimodipine or placebo group over the entire time course. Maximal vasodilation with 10% $CO_2$ increased the vessel diameters both at baseline and on day 13, but did not increase the vessel number on either occasion, indicating that all vessels were open. However, the vessel number of day 13 after nimodipine was significantly greater than that at baseline.

Figure 6:
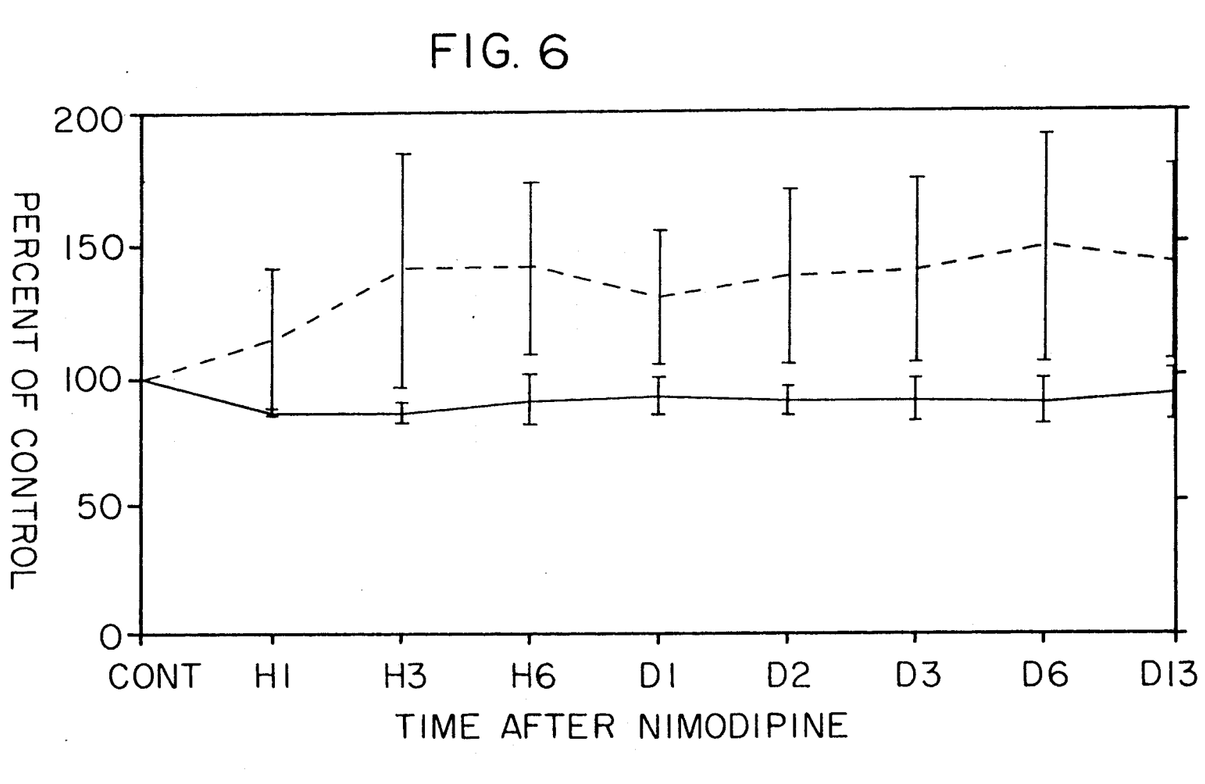
FIG. 6 is a graph demonstrating the effect of nimodipine on total length of the rat pial small arterioles over 13 days. There was a 47% increase in total length in the chronic epoch. Note no significant changes were seen in the placebo group. For notations see FIG. 1.
Figure 7:
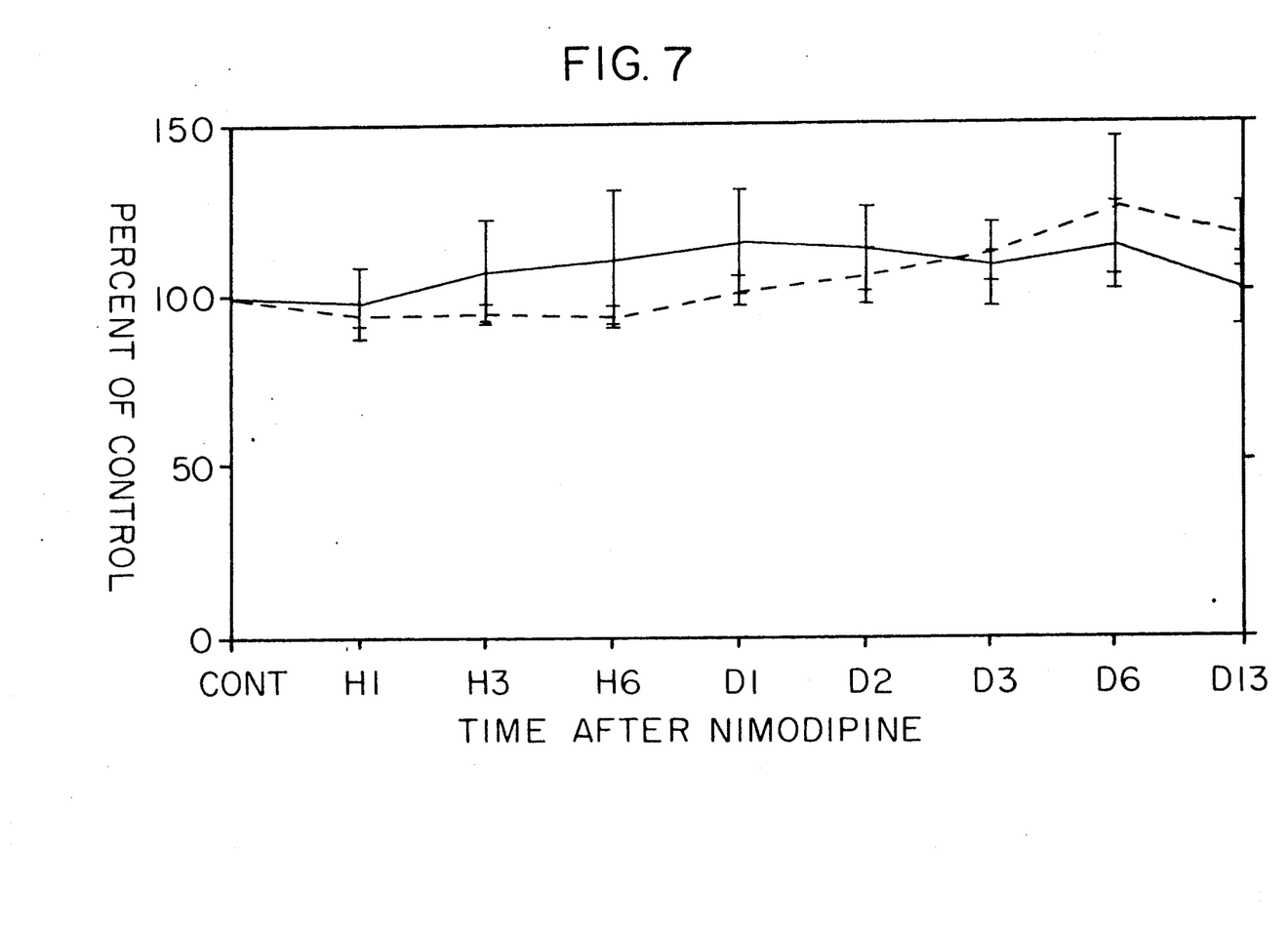
FIG. 7 is a graph demonstrating the effect of nimodipine on total length of the rat pial small venules over 13 days. There was a 23% (p<0.001) increase in total length in the chronic epoch. Note no significant changes were seen in the placebo group. For notations see FIG. 1.

The total length of small arterioles and venules increased 47% and 23% in the chronic epoch, respectively ($p < 0.001$, FIGS. 6 and 7). However, the average length of the small vessels did not change significantly. The increase in total length was brought about entirely by the increase in number of small vessels. In the placebo group, none of these vessels exhibited significant increases in length (FIGS. 6 and 7).

DISCUSSION

Animal Model

Direct observation of the surface vessels of the brain is a useful method for studying the cerebral circulation. The surface precapillary cerebral vessels account for a large portion of the total cerebral vascular resistance and their responses are generally representative of responses of the cerebral circulation as a whole. (Rosemblum W. I., and H. A. Kontos. The importance and relevance of studies of the pial microcirculation. Stroke 5: 425-428, 1974.) The cranial window technique has several advantages in studying this portion of the cerebral circulation. By restoring the integrity of the skull, it maintains an environment for the pial vessels as close to normal as possible with respect to intracranial pressure, composition of the surrounding fluid, and gas tensions. (Heistad D. D., and H. A. Kontos. Cerebral Circulation. In J. T. Shepherd and F. M. Abboud, Handbook of Physiology—The Cardiovascular System III; American Physiological Society, Bethesda, Md.; 1983, pp. 137-182.)

Most investigators who have worked with the pial microcirculation have utilized anesthetized animals because the animals must be still for microcirculatory measurements. Rarely have these investigator ventured into using cranial windows in the unanesthetized animals. However, one report in the literature from a very reputable group has demonstrated that the technique can be used in restrained rabbits. (Levasseur J. E., E. P. Wei, H. A. Kontos, and J. L. Patterson Jr. Responses of pial arterioles after prolonged hypercapnia and hypoxia in the awake rabbit. J. Appl. Physiol. 46: 89-95, 1979.) Yet no study of this kind has been reported in conscious rats, despite the fact that consciousness is important for the evaluation of normal vasoresponsiveness. The cranial window preparation we report afforded a very satisfactory view of a relatively large area of the surface of the rat's brain. It makes possible long-term measurements of the pial microvasculature in small, conscious animals that are not compromised by the effects of anesthesia. The window is simply a flat cover slip sealed over an accurately cut opening in the skull. This technique is a continued modification of the Smith pial window technique. (Smith T. C, D. Lynch, A. A. Khraibi, M. Levitt, and P. M. Hutchins. A pial window for microvascular observations in unanesthetized rats. Microvascular Research 29:251, 1985.) It differs from the Smith technique in the following manner: 1) we implanted a cover slip as opposed to using a bolted on chamber, 2) a superglue seal was used instead of a silicone rubber seal, 3) the cover slip rested on a cranial ledge, 4) the implant had a smaller total diameter, 5) our implant afforded greater microbial prophylaxis, and 6) had a much longer life span.

Although the concept is simple, the technique is intricate and time-consuming. The most common cause of failure is hemorrhage. Removal of the cut bone occasionally tears the sagittal sinus, causing complete failure of the preparation. However, minor bleeding from small cranio-dural arterioles torn in detaching the bone is naturally repaired in a day or two. Dural vessels are more likely to be cut, especially in the process of incising the dura at the lateral borders of the mid-sagittal sinus. Initially, lyophilized thrombin was applied to stop bleeding. However, removal of the resulting clot usually caused more bleeding. Therefore, we found it more effective to continually drip artificial cerebrospinal fluid onto the bleeding site until the bleeding completely stopped. In this way no external clot was formed. Because the cut bone edge might also bleed, it was important to be sure that no bleeding was in progress before sealing the chamber. Small hemorrhages also occurred occasionally shortly after surgery, usually on the first post-operative day; but in most cases the hemorrhage was of short duration and any blood beneath the coverslip would be absorbed rapidly and completely disappear in several days.

Other previously reported causes of failure might be: 1) ill-fitting or imperfect-sealed cover slips resulting in leakage of cerebrospinal fluid, 2) damage to the surface of the brain during removal of the dura, and 3) infection of the chamber. (Levasseur J. E., E. P. Wei, A. J. Raper, H. A. Kontos, and J. L. Patterson Jr. Detailed description of a cranial window technique for acute and chronic experiments. Stroke 6:308-317, 1975.) However, all of these can be prevented by being extremely meticulous and patient during the surgery. To date we have carried out chronic experiments in about 50 rats using the technique described above. Only one of them was considered a failure because of a defect in the preparation.

Nimodioine

Nimodipine has been the subject of considerable investigation in recent years. It appears to have several physiological effects that may be of benefit in the prevention or treatment of ischemia and stroke in the central nervous system. Our study showed a significant dilation of cerebral arterioles in the nimodipine treated group, whereas diameter changes among the large and small arterioles in the placebo group were not significant, indicating that changes in vessel caliber were brought about by the nimodipine rather than the implanted cranial window or other manipulations.

Autoregulation by the cerebral circulation is extremely effective. Cerebral arterioles respond to increases in arterial pressure with constriction and to decreases in arterial pressure with dilation. (Heistad D. D., and H. A. Kontos. Cerebral Circulation. In J. T. Shepherd and F. M. Abboud, Handbook of Physiology—The Cardiovascular System III; American Physiological Society, Bethesda, Md.; 1983, pp 137-182.) However, in our experiment it seems that the increase in pial vessel diameter was a direct effect of nimodipine. Autoregulation could not be implicated as a cause of the vasodilation, because in the nimodipine treated group there were increases in vessel caliber throughout the whole observation period without a significant decrease in systemic blood pressure. Moreover, significant vasodilation in arterioles occurred at hour 1 despite a significant (10%) increase in mean blood pressure, which should otherwise cause a cerebral vasoconstriction by autoregulatory means.

Subcutaneous administration of nimodipine caused an almost immediate dilation of cerebral arterioles, indicating nimodipine crosses the blood-brain barrier. This may be of benefit in the prevention of cerebral ischemia; but not necessarily for the treatment of lesions, because blood flow may not be increased preferentially to an injured area where the barrier has been damaged. (Harper A. M., L. Craigen, and S. Kazda. Effect of the calcium antagonist, nimodipine, on cerebral blood flow and metabolism in the primate. J. Cereb. Blood Flow Metab. 1: 349-356, 1981.)

Our results showed that nimodipine dilated large arterioles more than small ones (FIGS. 1 and 2). Since large arterioles account for a greater portion of vascular resistance in the brain than in other vascular beds, (Heistad D. D., and H. A. Kontos. Cerebral Circulation. In J. T. Shepherd and F. M. Abboud, Handbook of Physiology—The Cardiovascular System III; American Physiological Society, Bethesda, Md.; 1983, pp 137-182.) a greater dilation of the large arterioles should exert a relatively greater effect on cerebral vascular resistance than small arteriolar dilation. In addition, dilation of large arterioles may reduce the steal phenomenon that would occur during focal increases in metabolism. (Heistad D. D., and H. A. Kontos. Cerebral Circulation. In J. T. Shepherd and F. M. Abboud, Handbook of Physiology—The Cardiovascular System III; American Physiological Society, Bethesda, Md.; 1983, pp 137-182.) The increased dilation of large arterioles would also allow the smaller arterioles to exert autoregulatory changes more easily. Therefore, the protective effects of nimodipine on cerebral microcirculation are many faceted.

In our study, the arteriolar dilation was seen at different times during the whole observation period (13 days). However, considering the fact that the significant intergroup difference only occurred at Hour 1, it seems likely that nimodipine exerted its cerebral vasodilatory effect mainly in the acute epoch. This effect was to some extent similar to that of hydralazine, which in our previous study using the rat skeletal muscle backflap chamber, showed an arteriolar dilation for only the first 6 hours after subcutaneously administering the drug during a 6 day observation period. (Hutchins P. M., T. H. Marshburn, S. J. Maultsby, C. D. Lynch, T. L. Smith, and J. W. Dusseau. Long term microvascular response to hydalazine in spontaneously hypertensive rats. 1988, in press Hypertension.) However, the differences between the effects of the two drugs are apparent. In our previous study, hydralazine produced a temporary vasodilation with a profound lasting decrease in systemic blood pressure, indicating more extensive vasodilatory effects. (Koch-Weser J. Hydralazine. N. Engl. J. Med. 295: 320-323, 1976.) However, the dilatory effects of nimodipine are more selective to the cerebral vessels. (Harris R. J., N. M. Branston, L. Symon, M. Bayhan, and A. Watson. The effects of a calcium antagonist, nimodipine, upon physiological responses of the cerebral vasculature and its possible influence upon focal cerebral ischaemia. Stroke 13: 759-766, 1982.; Kazda S., R. Towart. Nimodipine: A new calcium antagonistic drug with a preferential cerebrovascular action. Acta Neurochirurgica 63: 259-265, 1982.; Towart R., E. Wehinger, H. Meyer, and S. Kazda. The effects of nimodipine, its optical isomers and metabolites on isolated vascular smooth muscle. Arzneimittelforsch 32:338-346, 1982.) Within the dosage range we used it renders a negligible effect on systemic blood pressure.

In the present study, venules showed a reduction in diameter. This indicates a fluid shift from the venuous side to the arterial side with no fluid retention. Fluid retention is a side effect of almost all vasodilators, and concerns many physicians using vasodilators to treat regional brain ischemia. Cerebral vasodilatation and fluid retention may cause an adverse effect on intracranial pressure. (Bedford R. F., R. Dacey, H. R. Winn, and C. Lynch III. Adverse impact of a calcium entry-blocker (verapamil) on intracranial pressure in patients with brain tumors. J. Neurosurg. 59: 800-802, 1983.) Therefore, our data support the findings that nimodipine exerts a cerebral vasodilatory effect without increasing intracranial pressure. (Hadley M. N., R. F. Spetzler, M. S. Fifield, W. D. Bichard, and J. A. Hodak. The effect of nimodipine on intracranial pressure. J. Neurosurg. 66: 387-393, 1987.)

Nimodipine is classified as a calcium channel blocker in its mechanism of action. Calcium plays an important role in the excitation-contraction coupling process of muscle. Smooth muscles contract by release of intracellular calcium and increased calcium influx from the extracellular space. (McCarron D. A. Is calcium more important than sodium in the pathogenesis of essential hypertension? Hypertension 1(5): 9-29, 1987; Przuntek H., F. V. Baumgarten, and H. G. Mertens. Treatment of vasospasm due to subarachnoid hemorrhage with calcium entry blockers. Eur. Neurol. 25(Suppl 1): 86-92, 1986; White B. C., C. D. Winegar, R. F. Wilson, P. J. Hoehner, and J. H. Trombley Jr. Possible role of calcium blockers in cerebral resuscitation: a review of the literature and synthesis for future studies. Crit. Care Med. 11: 202-207, 1983.) Under resting conditions the extracellular level of calcium is $10^{-3}$ M and the intracellular level $10^{-7}$ M. (Przuntek H., F. V. Baumgarten, and H. G. Mertens. Treatment of vasospasm due to subarachnoid hemorrhage with calcium entry blockers. Eur. Neurol. 25(Suppl 1): 86-92, 1986.) Hence, calcium ions are normally maintained with a 10,000-fold gradient from the extra- to intracellular space. (White B. C., C. D. Winegar, R. F. Wilson, P. J. Hoehner, and J. H. Trombley Jr. Possible role of calcium blockers in cerebral resuscitation: a review of the literature and synthesis for future studies. Crit. Care Med. 11: 202-207, 1983.) The intracellular level of free calcium must increase 100-fold to induce a muscle contraction. (Przuntek H., F. V. Baumgarten, and H. G. Mertens. Treatment of vasospasm due to subarachnoid hemorrhage with calcium entry blockers. Eur. Neurol. 25(Suppl 1): 86-92, 1986.)

Extracellular calcium is thought to play a larger role in vascular smooth muscle contraction than in myocardial or skeletal muscle contraction. (Murphy R. A. Contraction of muscle cells. IN R. M. Berne and M. N. Levy, Physiology 2nd ed; The C. V. Mosby Company; 1988, pp 315-342.) Furthermore, contraction of cerbral vessels is more dependent than those of systemic blood vessels on the inward movement of extracellular calcium. (Allen G. S., C. J. Gross, L. M. Henderson, and S. N. Chou. Cerebral arterial spasm. J. Neurosurg. 44: 585-593, 1976; Kazda S., R. Towart. Nimodipine: A new calcium antagonistic drug with a preferential cerebrovascular action. Acta Neurochirurgica 63: 259-265, 1982; McCalden T. A. Nimodipine and the cerebral circulation. Biblthca. cardiol. No 38 pp 244-249, 1984; Murphy R. A. Contraction of muscle cells. IN R. M.

Berne and M. N. evy, Physiology 2nd ed; The C. V. Mosby Company; 1988, pp 315–342.) Based on these basic physiologic features, the cerebral vascular selectivity for calcium entry blockers could be anticipated. This selectivity is very important for a vasodilator to be used in preventing or treating cerebral ischemia, because a generalized systemic hypotension induced by non-specific vasodilation would decrease cerebral blood flow. (Mohamed A. A., J. McCulloch, A. D. Mendelow, G. M. Teasdale, and A. M. Harper. Effect of the calcium antagonist nimodipine on local cerebral blood flow: Relationship to arterial blood pressure. J. Cereb. Blood Flow Metab. 4: 206–211, 1984.) A number of studies have attempted to show in vivo that calcium entry blockers produce relaxation of cerebral vessels and improve cerebral blood flow without simultaneous hypotensive effects. (McCalden T. A. Nimodipine and the cerebral circulation. Biblthca. cardiol. No 38 pp. 244–249, 1984.) However, verapamil produced an increased cerebral blood flow in the cat only when the hypotensive effect of the drug was controlled; (McCalden T. A. Nimodipine and the cerebral circulation. Biblthca. cardiol. No 38 pp 244–249, 1984) thus, limiting its use in improving cerebral blood flow. The 20 mg pellets we implanted subcutaneously, have been shown by the manufacturer to release a constant dose over 21 days. For a 300 gram rat a release rate of 2.20 $\mu g/kg/min$ could be roughly estimate. At this rate, marked cerebral vasodilation was seen in the very beginning without a significant decrease in systemic blood pressure. This strongly indicates a selective or specific action of nimodipine on the cerebral vasculature. However, the specificity of nimodipine is not invariable; it varies with the dosage given. In one study with nimodipine in the baboon, (McCalden T. A. Nimodipine and the cerebral circulation. Biblthca. cardiol. No 38 pp 244–249, 1984) 0.1 $\mu g/kg/min$ intravenously produced no significant alteration in cerebral blood flow, arterial blood pressure or cerebral vascular resistance. At an infusion rate of 1.0 $\mu g/kg/min$, an increase in cerebral blood flow with no change in blood pressure was found, indicating a cerebral vaporization. At higher dosages (>1.0 $\mu g/kg/min$) the increase in cerebral blood flow was attenuated while blood pressure fell. Therefore, the balance between the hypotensive effects on systemic arterial blood pressure and cerebral vasodilation seems critical. In order to achieve cerebral vasodilation without induced systemic hypotension a large dosage is not only unnecessary but also contraindicated because the high level of nimodipine would dilate the peripheral vasculature. (Ment L. R., W. B. Stewart, C. C. Duncan, and B. R. Pitt. Beagle pup model of perinatal asphyxia: Nimodipine studies. Stroke 18: 599–605, 1987; Takata Y., and H. Kato. Comparative study on acute antihypertensive effects and pharmacokinetics of nisoldipine, nifedipine, nimodipine and nicardipine administered orally to conscious renal hypertensive dogs. Arzneimittelforsch 36(II): 1464–1471, 1986.)

Based on the animal model, and experience with administration of nimodipine for other cerebral indications such as subarachnoid hemorrhage and cerebral stroke, doses of about 0.5 to 4.0 mg per kg of body weight per day for a period of greater than 6 days is in the range for an effective amount of nimodipine. Individual doses may range from 100–500 mg per day for periods of 7–21 days, with 14 days being an average length of time.

Vessel Growth

Our study showed a marked increase in the number of small arterioles and the length of all vessels throughout the observation period. This may be due to the opening of previously closed vessels by the drug, or new vessel growth. Since the $CO_2$ study excluded the former possibility, the vessel number increase in our experimental conditions meant vessel growth. New vessel growth can happen within a few days. (Guyton A. C. Local control of blood flow by the tissues, and nervous and humoral regulation. In A. C. Guyton,Textbook of Medical Physiology 7th ed; W. B. Saunders Company; 1986, pp 230–243.) As the effect of nimodipine continued, vasodilation might be combined with or replaced by increased vessel growth. It is most likely that in the present experiment, the main long-term effects of nimodipine on the pial microcirculation is causing vessel growth. Since the small vessel average length did not change significantly, the longitudinal vessel growth would not increase the cerebral vascular resistance; instead, the resistance would be reduced by an increased number of vessels in parallel.

It has long been considered that hypoxia and a resultant release of metabolites are major factors supporting new blood vessel growth. (Dusseau J. W., and P. M. Hutchins. Hypoxia-induced angiogenesis in chick chorioallantoic membranes: a role for adenosine. Respiration Physiology, 71: 33–44, 1988; Guyton A. C. Local control of blood flow by the tissues, and nervous and humoral regulation. In A. C. Guyton, Textbook of Medical Physiology 7th ed; W. B. Saunders Company; 1986, pp 230–243.) However, no hypoxic situation existed in our experiment, and no other chemical factors except calcium were directly involved. Based on our literature search no study has been reported on the direct relationship between angiogenesis (excluding mitosis) and calcium or a calcium channel blocker. Therefore, a possible explanation of the mechanism responsible for the vessel growth seen in our experiment would be mechanical factors. It has been observed that capillaries with higher blood flow have more sprouts and gradually change into arterioles and venules, while those with low flow gradually narrow and disappear. (Hudlicka 0. Development of microcirculatio: capillary growth and adaptation. In E. M. Renkin and C. C. Michel, Handbook of physiology—The cardiovascular system IV: American Physiological Society, Bethesda, Md.; 1984, pp 165–216.) Indeed, vasodilation and the resultant increased regional blood flow and blood pressure in terminal vessels have recently been considered a common denominator of many conditions leading to vessel proliferation. (Hudlicka 0. Development of microcirculation: capillary growth and adaption. In E. M. Renkin and C. C. Michel, Handbook of physiology—The cardiovascular system IV; American PhysiologicalSociety, Bethesda, Md.; 1984, pp 165–216; Mall G., I. Schikora I, T. Mattfeldt, and R. Bodle. Dipyridamole-induced neoformation of capillaries in the rat heart. Laboratory Investigation 57: 86–93, 1987; Sastre N., A. Rodriguez, and R. Blas. Skin flap neovascularization by means of a vasodilator. J Reconstructive Microsurgery 3: 265–268, 1987; Tornling G. Capillary neoformation in the heart of dipyridamole-treated rats. Acta Path. Microbiol. Immunol. Scand. Sect. A90: 269–271, 1982; Wright A. J. A., O. Hudlicka, K. R. Tyler, and A. Ziada. The effect of vasoactive drugs on capillary density and performance in skeletal muscles. Biblthca Anat. No 20, 1981 pp 362–365; Ziada A. M., O. Hudlicka, K. R. Tyler, and A. J. A. Wright. The effect of long-term vasodilatation on capillary growth and performance in rabbit heart and skeletal muscle. Cardiovascular Research 18: 724–732, 1984.) It has been suggested that vasodilation leads to increased tangential vessel wall stress, which in turn triggers a proliferation of wall cells. (Mall G., I. Schikora I. T. Mattfeldt, and R. Bodle. Dipyridamole-induced neoformation of capillaries in the rat heart. Laboratory Investigation 57: 86–93, 1987; Tornling G, J. Adolfsson, G. Unge, and A. Ljungqvist. Capillar neoformation in skeletal muscle of dipyridamole-treated rats. Arzneimittelforsch 30(1): 791–792, 1980. Such a mechanism would be consistent with the vessel proliferation seen in the present study.

A new technique for long-term, longitudinal observations of the pial microvasculature in conscious rats is presented. This model avoids the confounding effects of anesthesia and acute operative manipulations on pial microvascular observations. In addition, the present experiment demonstrated that the subcutaneous administration of 20 mg of nimodipine in conscious rats caused a short term arteriolar dilation without significant systemic hypotension, and results in new vessel growth in the long-term. The blood-brain barrier was not a problem for drug efficacy. Nimodipine did not seem to have a fluid retention effect as has been shown with many other vasodilators. These pharmacologic properties may be of benefit in the prophylaxis of treatment cerebral ischemia and stroke.

TABLE 1

EFFECTS OF NIMODIPINE AND PLACEBO ON MAP AND HR IN RATS

|     |   | 24 HOUR AVERAGE | CONTROL | HOUR 1 | HOUR 3 | HOUR 6 | DAY 1 |
|-----|---|-----------------|---------|--------|--------|--------|-------|
| MAP | N | 110.4 ± 3.7 | 100 | 109.6 ± 1.8$^d$ | 108.1 ± 1.7$^c$ | 107.7 ± 1.2$^d$ | 102.1 ± 1.6 |
|     | P | 102.7 ± 2.1 | 100 | 114.9 ± 2.2$^b$ | 111.8 ± 2.4$^b$ | 114.3 ± 1.4$^c$ | 104.4 ± 2.5 |
| HR  | N | 329.4 ± 4.2   A | 100 | 121.7 ± 2.7$^d$ | 116.1 ± 2.5$^d$ | 112.2 ± 1.7$^d$ | 101.0 ± 0.8 |
|     | P | 315.7 ± 6.9 | 100 | 129.4 ± 4.8$^c$ | 116.7 ± 4.7$^a$ | 115.5 ± 3.3$^b$ | 100.3 ± 2.3 |

|     |   | DAY 2 | DAY 3 | DAY 6 | DAY 13 |
|-----|---|-------|-------|-------|--------|
| MAP | N | 101.6 ± 2.3 | 101.2 ± 2.1 | 98.7 ± 2.3 | 97.3 ± 2.7 |
|     | P | 105.5 ± 2.8 | 103.5 ± 2.5 | 105.6 ± 1.9$^a$ | 105.3 ± 1.1$^b$ |
| HR  | N | 99.3 ± 1.4 | 100.1 ± 1.4 | 97.2 ± 1.6$^a$ | 93.7 ± 1.3$^b$ |
|     | P | 101.9 ± 0.7$^a$ | 101.8 ± 0.8$^a$ | 98.7 ± 1.8 | 96.2 ± 0.8$^b$ |

24-hour average is absolute values; all the other values are percent of control
MAP = mean arterial pressure (mmHg); HR = heart rate (beats/min)
N = Nimodipine group; P = Placebo group.
Intragroup difference (compared to control): $^a p < 0.05$; $^b p < 0.01$; $^c p < 0.001$; $^d p < 0.0001$
Intergroup difference: A. $p < 0.05$

What is claimed is:

1. A method of increasing cranial vessel growth in warm-blooded animals comprising administering an effective amount of nimodipine to said animals subcutaneously or locally to achieve vessel proliferation.

2. The method of claim 1 wherein nimodipine has the formula: 1,4-dihydro-2,6-dimethyl-4-(3'-nitrophenyl)-pyridine-3-($\beta$-methoxyethyl ester)-5-(isopropyl ester).

3. The method of claim 2 in which the active compound is administered to deliver an effective amount of about 0.5 to 4.0 mg per kg body weight per day for greater than 6 days.

4. The method of claim 3 wherein the effective amount is about 3.0 mg per kg body weight per day for at least 14 days.

* * * * *